United States Patent [19]

Wandell

[11] Plant 5,221

[45] Apr. 17, 1984

[54] GINKGO TREE NAMED SHANGRI-LA

[76] Inventor: Willet N. Wandell, Myra Station Rd., Rte. 3, Box 158, Urbana, Ill. 61801

[21] Appl. No.: 245,154

[22] Filed: Mar. 18, 1981

[51] Int. Cl.[3] ..... A01H 5/00
[52] U.S. Cl. ..... Plt./51
[58] Field of Search ..... Plt./51

[56] References Cited

U.S. PATENT DOCUMENTS

P.P. 2,675 10/1966 Flemer ..... Plt./51

OTHER PUBLICATIONS

Preston, R. J., *North American Trees,* printed by the Iowa State College Press pp. 50 and 51, (date 1950).

Graves, A. H., *Illustrated Guide to Trees and Shrubs* Harper and Brothers, Publishers, N.Y., (1956), pp. XI--XIII.

*Primary Examiner*—James R. Feyrer
*Attorney, Agent, or Firm*—Wm. A. Snow

[57] ABSTRACT

A new and distinct variety of cultivar of Ginkgo tree of the *Ginkgo biloba* type characterized by a more compact habit of growth and a more desirable arrangement of branches growing at a favorable angle from the trunk and the crown having a full, dense, moderate spread.

3 Drawing Figures

SUMMARY OF THE INVENTION

This variety of the Ginkgo tree type was discovered by me in 1963 in a planting of seedlings in Urbana, Ill., on cultivated property. During the past several years, I have rooted vegetative cuttings in my greenhouse under a mist at Urbana, Ill., and also have propagated it by grafting onto seedling understock or by soft wood cuttings. At the present time, I have about 700 of these trees growing true to form. They are rapid growers even as a juvenile and are outstanding.

BRIEF DESCRIPTION OF THE DRAWINGS

The upper photograph shows my new variety as it appears with full foliage.

The lower photograph is the new variety without foliage.

The pen-and-ink drawing discloses the mature leaves, stems and buds.

DETAILED DESCRIPTION OF THE NEW PLANT

The following is a detailed description of my new hybrid Ginkgo tree, the stated observations having been made of trees growing at Urbana, Ill.

Origin: Seedling.
Parentage: Varient of *G. biloba.*
Classification: *Ginkgo biloba.*
Propagation: Holds its distinguishing characteristics through succeeding propagation both by rooting, vegetative cuttings and grafting understook or soft wood cuttings.
Form: Tree.
Shape: Robust, moderately spreading and dense crown on male.
Height: Upright about 55 feet, robust, straight upright trunk.
Trunk size: 18.2 Inches in diameter of mature tree.
Growth rate: Relatively fast growing for species.
Bark: Dark to light grey and heavily furrowed exposing tan colored bark at bottom of furrows.
Branches: Numerous, dark to light grey, with older branches scaly; new twigs straight, moderate 3–4 mm. in diameter, round glabrous, light tan-brown with lateral spurs up to 1.5 mm. long.
*Angle of attachment.*—Oblique at 50° angle. Borne alternate or clustered on spurs. Spread 40 feet after 17 years, the basic scaffold, and the supplementary or secondary branches, occur throughout the center of the crown giving the tree crown a heavy, full appearance.
*Size.*—9 cm.
*Spacing.*—12.7 cm.
Leaves: Mature.
*Length.*—3.5–6 cm.
*Width.*—At broadest part, 5–10 cm.
*Form.*—Fan or web shaped with broad upper margin irregularly repand and often with one deeper cleft.
*Veins.*—Dichotomously branched from base.
*Petioles.*—3.5 to 8 cm. long.
*Pubescence distribution.*—None.
*Quantity.*—Abundant.
Winter buds: Solitary, sessile, terminating the spurs, broad-conical, 3 mm. long, with 3–5 imbricate bud scales.
Flowers: Male; long staminate catkin, not ornamental.
*Quantity.*—Normal.
*Size.*—Normal. Length: 3.4 cm. to 3.8 cm. Width: 0.8 cm.
Fruit: None due to male sex completely free from usual foul odor of ripe fruit normal in the female of the species.

This variety resembles *Ginkgo biloba* and clearly distinguishes from other Ginkgo trees by the rapid growth habit growing to 55 feet in height with a branch spread of 40 feet after 17 years of growth; dense in addition to the basic scaffold, supplementary or secondary branches occur throughout the center of the crown giving it a heavy, full crown, even as a juvenile having grown 55 feet with a branch spread of 40 feet; favorable angle at which the branches are produced on the trunk; balanced, moderately spreading crown; and male flower characteristics. All the above stated characteristics and distinctions come true and are propagated and transmitted in succeeding propagations.

I claim:

1. A new and distinct variety of *Ginkgo biloba,* substantially as herein shown and described, characterized by its rapid, compact growth habit growing 55 feet in height with a 40 foot branch spread in 17 years, dense full crown caused by in addition to the basic scaffold, the supplementary or secondary branches occurring throughout the center of the crown giving the tree crown a heavy, full appearance, straight trunk, ease of propagation and freedom from production of foul smelling fruit.

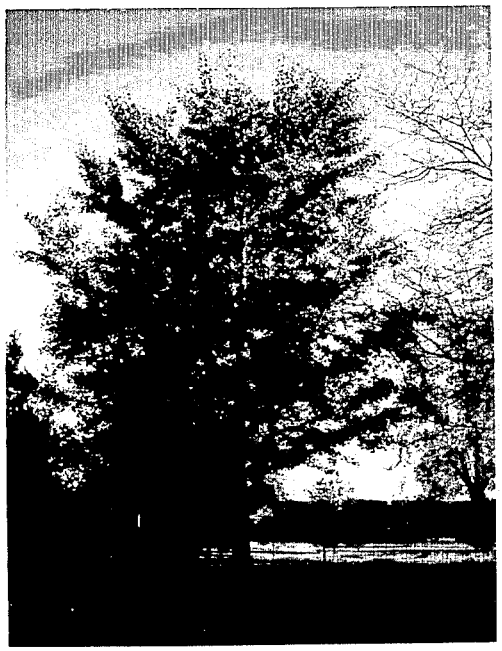
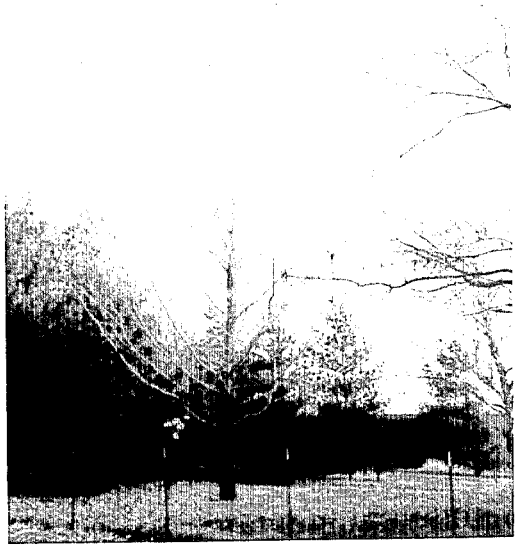

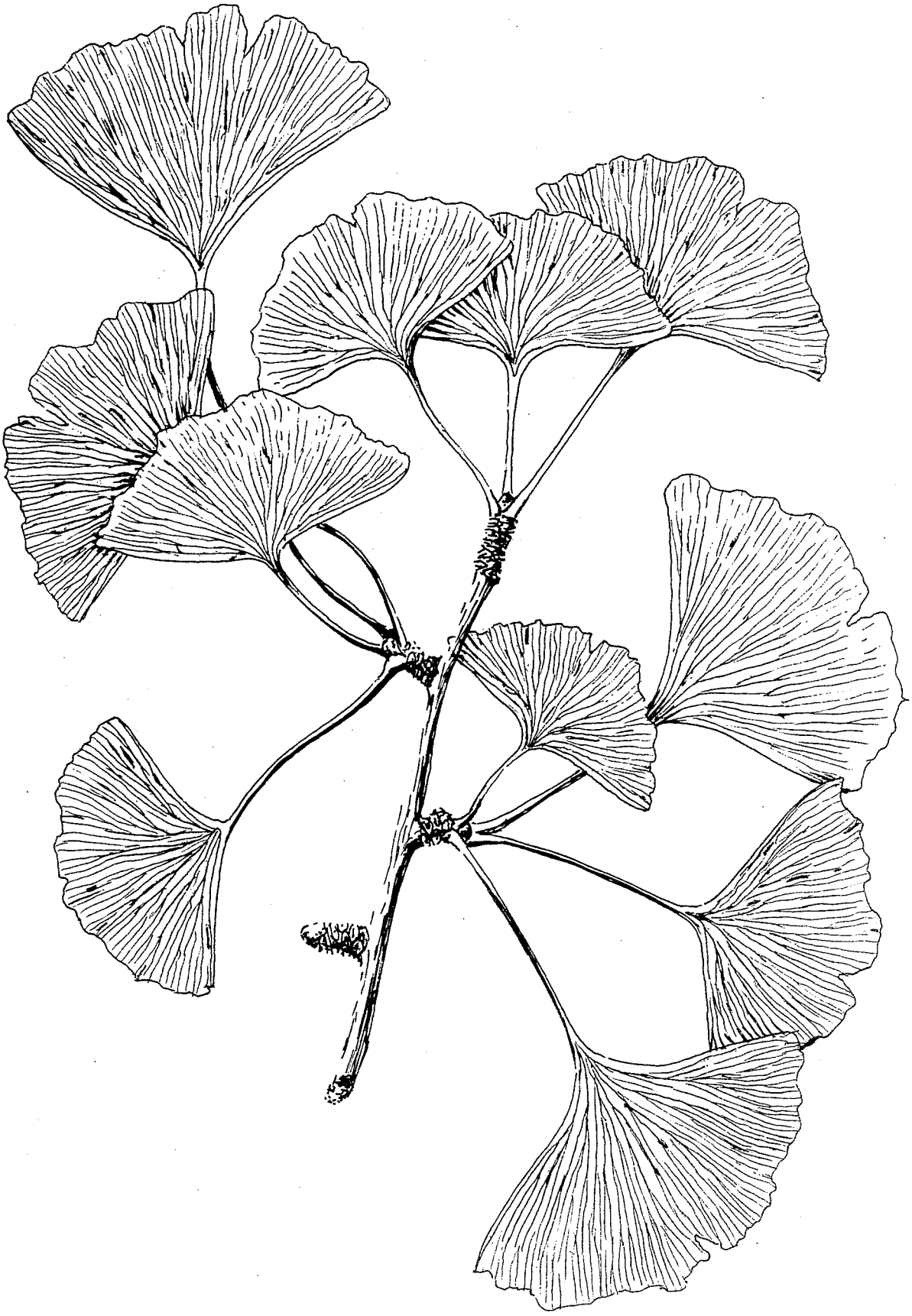

* * * * *